(12) United States Patent
Shalev et al.

(10) Patent No.: US 8,241,913 B2
(45) Date of Patent: Aug. 14, 2012

(54) VIRTUAL SEMICONDUCTOR NANOWIRE, AND METHODS OF USING SAME

(75) Inventors: Gil Shalev, Ramat Hashoron (IL); Amihood Doron, Ahuzat-Barak (IL); Ariel Cohen, Givat Yearim (IL)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 13/216,005

(22) Filed: Aug. 23, 2011

(65) Prior Publication Data

US 2011/0304317 A1 Dec. 15, 2011

Related U.S. Application Data

(62) Division of application No. 12/156,361, filed on May 30, 2008, now Pat. No. 8,007,727.

(51) Int. Cl.
*G01N 15/06* (2006.01)
*G01N 33/00* (2006.01)
*G01N 33/48* (2006.01)

(52) U.S. Cl. ............ 436/43; 422/68.1; 422/50; 422/83; 422/82.01; 422/82.02; 436/63; 436/149; 436/151

(58) Field of Classification Search .................. 436/43, 436/149, 151; 422/50, 68.1, 83, 82.01, 82.02
See application file for complete search history.

(56) References Cited

U.S. PATENT DOCUMENTS

| 4,241,316 | A | 12/1980 | Knapp |
| 4,496,909 | A | 1/1985 | Knapp |
| 7,018,901 | B1 | 3/2006 | Thean et al. |
| 7,067,868 | B2 | 6/2006 | Thean et al. |
| 7,495,290 | B2 | 2/2009 | Li |
| 7,525,160 | B2 | 4/2009 | Kavalieros et al. |
| 7,595,244 | B1 | 9/2009 | Bulucea et al. |
| 7,611,943 | B2 | 11/2009 | Liu |
| 7,632,745 | B2 | 12/2009 | Chen |
| 7,701,005 | B1 | 4/2010 | Bulucea et al. |
| 7,749,832 | B2 | 7/2010 | Li |
| 7,759,179 | B2 | 7/2010 | Anderson et al. |

OTHER PUBLICATIONS

Akarvardar et al., "Depletion-All-Around Operation of the SOI Four-Gate Transistor", IEEE Transactions on Electron Devices, vol. 54, No. 2, Feb. 2007, pp. 323-331.
Chen et al., "SOI four-gate transistors (G4-FETs) for high voltage analog applications", In Proceedings of the 31st European Solid-State Circuits Conference (ESSCIRC), Sep. 2005, pp. 311-314.
Stern et al., "Label-free immunodetection with CMOS-compatible semiconducting nanowires", vol. 445, Feb. 1, 2007, Nature, pp. 519-522.

*Primary Examiner* — Brian J Sines
(74) *Attorney, Agent, or Firm* — Winkle, PLLC

(57) ABSTRACT

A multiple-gate field-effect transistor includes a fluid in a top gate, two lateral gates, and a bottom gate. The multiple-gate field-effect transistor also includes a patterned depletion zone and a virtual depletion zone that has a lesser width than the patterned depletion zone. The virtual depletion zone width creates a virtual semiconductor nanowire that is lesser in width than the patterned depletion zone.

5 Claims, 4 Drawing Sheets

VIRTUAL SEMICONDUCTOR NANOWIRE, AND METHODS OF USING SAME

RELATED APPLICATIONS

This is a Divisional of patent application Ser. No. 12/156,361, filed on May 30, 2008, now U.S. Pat. No. 8,007,727.

TECHNICAL FIELD

Disclosed embodiments relate to semiconductive apparatus and methods of using them.

BRIEF DESCRIPTION OF THE DRAWINGS

In order to understand the manner in which embodiments are obtained, a more particular description of various embodiments briefly described above will be rendered by reference to the appended drawings. These drawings depict embodiments that are not necessarily drawn to scale and are not to be considered to be limiting in scope. Some embodiments will be described and explained with additional specificity and detail through the use of the accompanying drawings in which.

DETAILED DESCRIPTION

A multiple-gate field-effect transistor (MUGFET) includes a fluid top gate to receive a biological product, and the MUGFET also includes a virtual depletion zone within a patterned depletion zone. The virtual depletion zone has a width that is less than the patterned depletion zone.

The following description includes terms, such as upper, lower, first, second, etc. that are used for descriptive purposes only and are not to be construed as limiting. The embodiments of an apparatus or article described herein can be manufactured, used, or shipped in a number of positions and orientations.

Reference will now be made to the drawings wherein like structures may be provided with like suffix reference designations. In order to show the structures of various embodiments most clearly, the drawings included herein are diagrammatic representations of integrated circuit structures. Thus, the actual appearance of the fabricated structures, for example in a photomicrograph, may appear different while still incorporating the claimed structures of the illustrated embodiments. Moreover, the drawings show only the structures necessary to understand the illustrated embodiments. Additional structures known in the art have not been included to maintain the clarity of the drawings.

Figure 1:
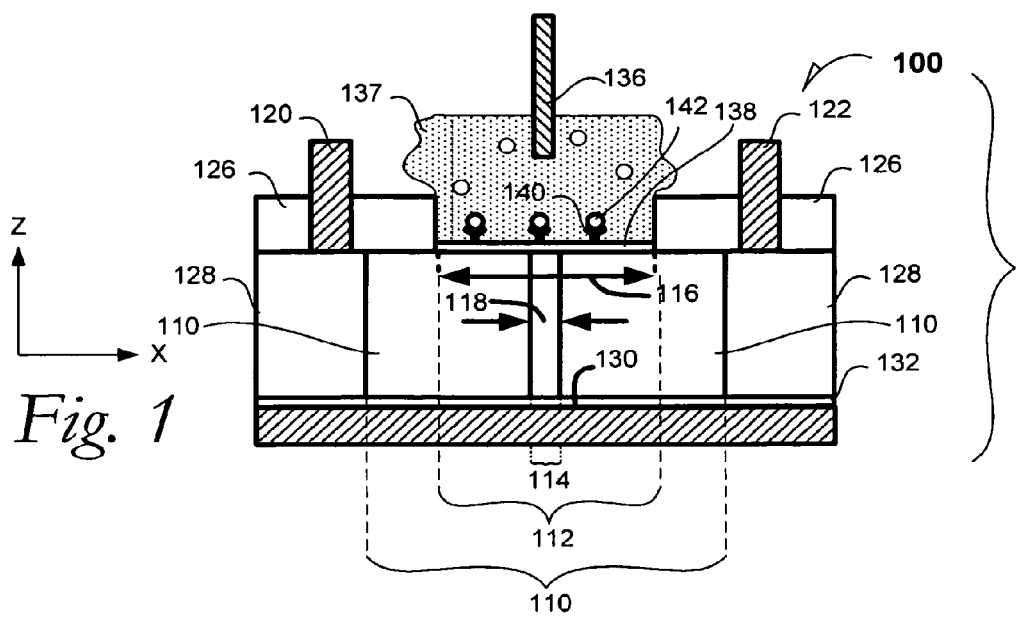
FIG. 1 is a cross-section elevation of a multiple-gate field-effect transistor according to an embodiment.

FIG. 1 is a cross-section elevation of a multiple-gate field-effect transistor (MUGFET) 100 according to an embodiment. A semiconductive well 110 includes a patterned depletion zone 112 and a virtual depletion zone 114. The patterned depletion zone 112 includes a first width 116 and the virtual depletion zone 114 includes a second width 118. During operation of the MUGFET, the second width 118 is less than the first width 116.

The MUGFET 100 also includes a first lateral gate 120 and a second lateral gate 122. The respective first- and second lateral gates 120 and 122 are connected to the diffusion terminals 128. The respective first- and second lateral gates 120 and 122 may be situated with a passivation layer 126 such as a polyimide material or a polyamide material. Other materials may be used for the passivation layer 126.

In an embodiment, the semiconductive well 110 is part of a larger semiconductive structure such as an epitaxial semiconductor material or a semiconductor on insulator (SOI) material. In an embodiment, the semiconductive well 110 is differently doped than lateral structures such as lateral implant regions 128.

In an embodiment, a bottom gate 130 is disposed below the semiconductive well 110 and it is insulated from the semiconductive well 110 with a bottom gate dielectric 132. In an embodiment, the bottom gate 130 is metallic. In an embodiment, the bottom gate 130 is polycrystalline.

In an embodiment, a reference electrode 136 interface the electrically conductive fluid 137 and acts as the top gate includes a top electrode. The electrically conductive fluid 137 may be a liquid or a vapor or a gas. Capture molecules 140 are coupled on the dielectric layer, 138. Additionally, the top gate includes an electrically conductive fluid 137 that immerses the capture molecule 140 and at least a portion of the top electrode 136. In an embodiment, the capture molecule 140 is a specific receptor for a biological product such as an antibody that has been developed to adhere to the top gate dielectric 138 and to be selective for capturing only analytes. Consequently, a label-free protein analysis method is achieved by using the MUGFET 100 with a virtual channel 114 that is the virtual depletion zone. In an embodiment, the system of analyte and capture molecule may be complementary type such as an organic system or an inorganic system.

The virtual depletion zone 114 fits entirely within the confines of the patterned depletion zone 112, and that has a virtual width 118 that is less than the patterned width 116. In an embodiment, a material such as a DNA sample is bonded to the capture molecule 140 in such a way that a given DNA sequence is identified. For example, the capture molecule 140 may be a complementary sequence for a DNA segment in electrically conductive fluid 137. In an example embodiment, immunosensing is performed where the capturing molecule is an antibody. In this example the analyte can be any molecule with antibody-antigen affinity such as prostrate specific antigen (PSA) or breast cancer (BRC).

FIG. 1 also depicts a specific analyte 142 one of which is referenced with the reference numeral 142. The specific analyte 142 has been captured by the capture molecule 140 such that performance of the MUGFET 100 is affected by the amount of analyte 142 that has been captured. For example, the potential that may be experienced by the MUGFET 100 at given overall amount of gate current and/or gate potential, can allow quantitative analysis of the presence of the analyte 142. In an embodiment, the analyte 142 binds with a carrier such as a light-active composition, and the presence of the analyte 142 is measured by optical analysis in relationship to the top gate.

In an embodiment, operation of the MUGFET 100 is carried out such that the virtual depletion zone 114 forms a virtual semiconductor nanowire 114 between a source and drain in the patterned depletion zone 112 of the MUGFET 100. The virtual width 118 of the virtual semiconductor nanowire 114 is less than the patterned width 116 in the semiconductive well 110. The virtual semiconductor nanowire 114 may have a more useful sensitivity to current and potential than the MUGFET with only the patterned width 116. This enhanced sensitivity may allow for more useful analysis of biological products.

In an embodiment, the patterned width 116 is in a range from about 2 nanometers (nm) to about 50 nm, and the virtual semiconductor nanowire 114 has a virtual width 118 that is less than the patterned width 116. For example, where the patterned width 116 of the patterned depletion zone 112 is unity, the virtual width 118 is about 20% of the patterned width. In an embodiment, where the patterned width 116 of the patterned depletion zone 112 is unity, the virtual width 118 is about 40% of the patterned width. In an embodiment, where the patterned width 116 of the patterned depletion zone 112 is unity, the virtual width 118 is about 60% of the patterned width. In an embodiment, where the patterned width 116 of the patterned depletion zone 112 is unity, the virtual width 118 is about 80% of the patterned width. In an embodiment, where the patterned width 116 of the patterned depletion zone 112 is unity, the virtual width 118 is about 10% of the patterned width. In an embodiment, the patterned width 116 is in a range from about 50 nm to about 250 nm.

Figure 2:
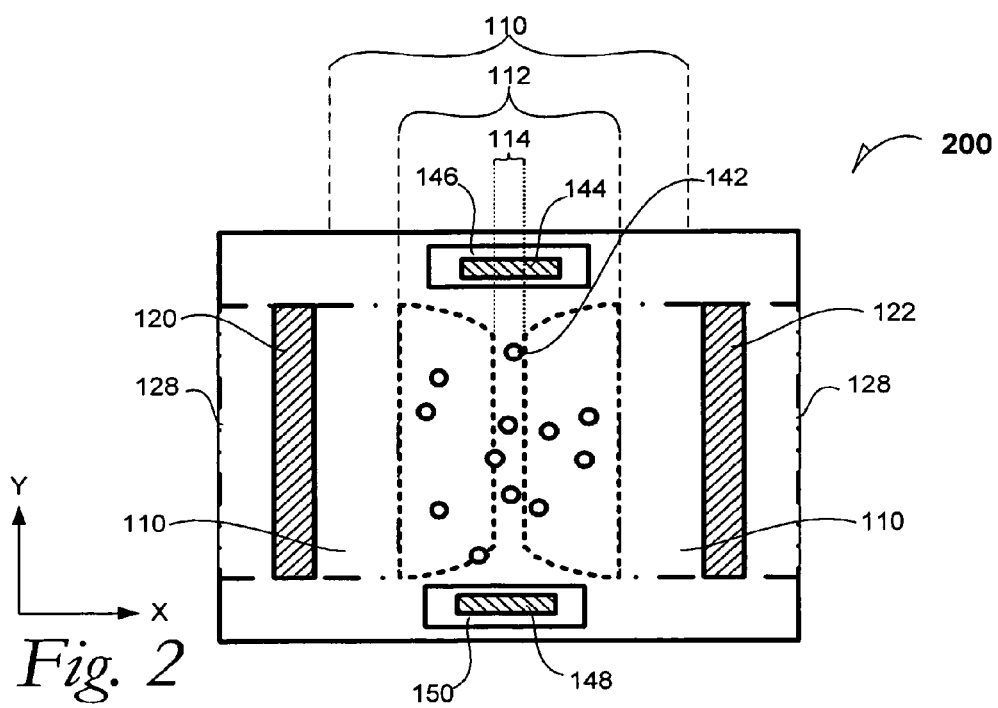
FIG. 2 is a top plan of the multiple-gate field-effect transistor depicted in FIG. 1 according to an example embodiment.

FIG. 2 is a top plan of the multiple-gate field-effect transistor 100 depicted in FIG. 1 according to an example embodiment. The semiconductive well 110 includes the patterned depletion zone 112 and the virtual depletion zone 114. The MUGFET 100 also includes the first lateral gate 120 and the second lateral gate 122. The respective first- and second lateral gates 120 and 122 are disposed above the lateral implant regions 128, which are depicted in phantom lines since they are obscured by the passivation layer 126 (FIG. 1).

A MUGFET source electrode 144 is depicted in contact with a source region 146, and a MUGFET drain electrode 148 is depicted in contact with a drain region 150.

During operation of the MUGFET 100, analyte 142 are interacting with a capture molecule (see FIG. 1). According to an embodiment, analysis for the analyte 142 is focused only on analyte 142 that has adsorbed onto capture molecules that are above the virtual depletion zone 114. Consequently, analysis of the content of biological products in the fluid portion 137 of the top gate is carried out. Because analysis is restricted to adsorbed analyte 142 only above the virtual depletion zone 114, the analysis may be more useful than when analysis is carried out above the entire patterned depletion zone 112. In FIG. 2 it can be seen that there are four analytes 142 above the virtual depletion zone 114, one occurrence of which is noted with the reference number 142.

Figure 3A:
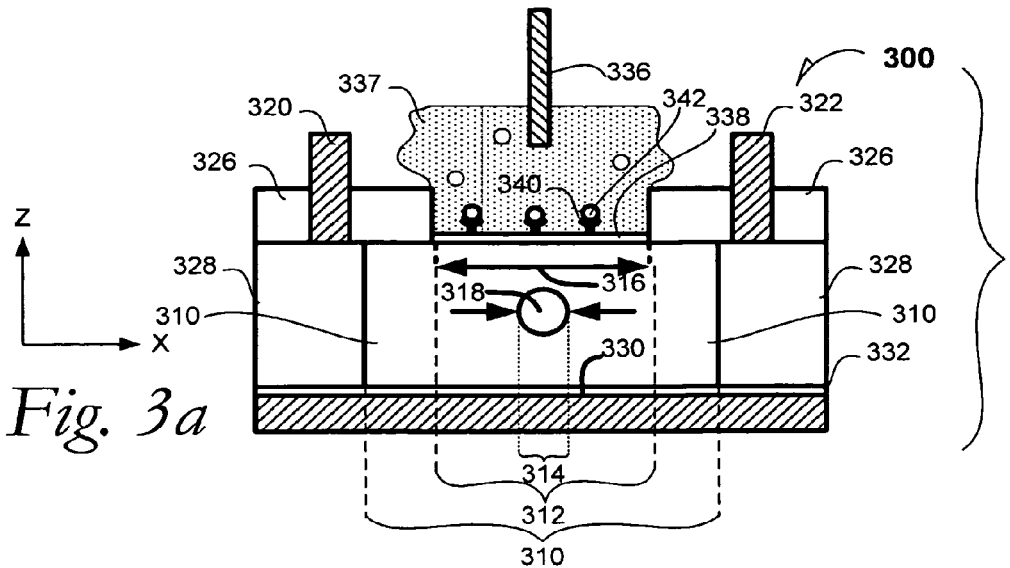
FIG. 3a is a cross-section elevation of a multiple-gate field-effect transistor according to an embodiment.

FIG. 3a is a cross-section elevation of a multiple-gate field-effect transistor 300 according to an embodiment. A semiconductive well 310 includes a patterned depletion zone 312 and a virtual depletion zone 314 that forms an arbitrary cross section; in the illustration, the arbitrary cross section is circular. The patterned depletion zone 312 includes a first width 316 and the virtual depletion zone 314 includes a second width 318. During operation of the MUGFET 300, the second width 318 is less than the first width 316. Consequently, a virtual semiconductor nanowire exists in the form of the virtual depletion zone 314 that has been imposed within the patterned depletion zone 312.

The MUGFET 300 also includes a first lateral gate 320 and a second lateral gate 322. The respective first- and second lateral gates 320 and 322 are that rests upon a top surface of the semiconductive material that includes the semiconductive well 310. The respective first- and second lateral gates 320 and 322 may be situated with a passivation layer 326 such as a polyimide material or a polyamide material. Other materials may be used for the passivation layer 326.

In an embodiment, the semiconductive well 310 is part of a larger semiconductive structure such as an epitaxial semiconductor material or a semiconductor on insulator (SOI) material. In an embodiment, the semiconductive well 310 is differently doped than lateral structures such as a lateral implant regions 328.

In an embodiment, a bottom gate 330 is disposed below the semiconductive well 310 and it is insulated from the semiconductive well 310 with a bottom gate dielectric 332. Vertical positioning of the virtual depletion zone 314 within the semiconductive well 310, as well as lateral dimensions of the virtual depletion zone 314 may be affected by the bottom gate 330 as well as the other gates 320, 322, and the top gate.

In an embodiment, the top gate includes a top electrode 336, a top gate dielectric 338, and a capture molecule 340. Additionally, the top gate includes an electrically conductive fluid 337 that immerses the capture molecule 340 and at least a portion of the top electrode 336.

Figure 3B:
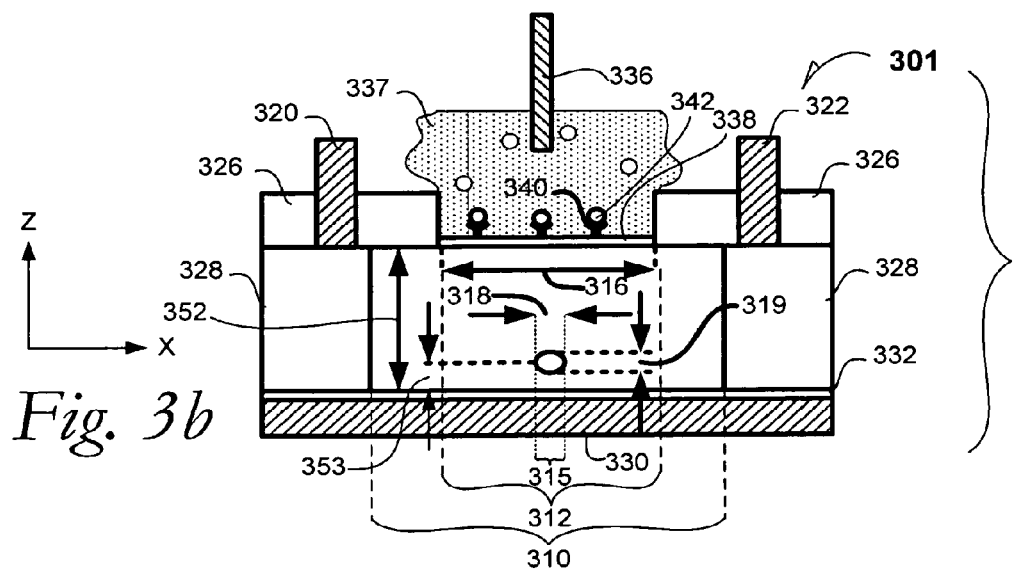
FIG. 3b is a cross-section elevation of the multiple-gate field-effect transistor depicted in FIG. 3a during a method according to an embodiment.

FIG. 3b is a cross-section elevation of the multiple-gate field-effect transistor 300 depicted in FIG. 3a during a method according to an embodiment. The MUGFET 301 is being operated such that the virtual depletion zone 315 has taken on a different oval shape in compared to the virtual depletion zone 314 depicted in FIG. 3a. Consequently, an oval-shaped virtual semiconductor nanowire exists in the form of the virtual depletion zone 315 that has been imposed within the patterned depletion zone 312.

In an embodiment, the semiconductive well 310 has a characteristic height 352 and the virtual depletion zone 315 is centered at a virtual depletion zone height 353. As illustrated and in an embodiment, the virtual depletion zone height 353 is below the middle of the characteristic height 352 of the semiconductive well 310. This location of the depletion zone height 353 may be referred to as "non-symmetrically vertical". In an embodiment, background and operational signal noise is reduced during analytical use of the MUGFET 301 when the virtual depletion zone height 353 is below the middle of the characteristic height 352 of the semiconductive well 310 (not necessarily below middle!). This location of the depletion zone height 353 may also be referred to as "non-symmetrically vertical".

In an embodiment, the virtual depletion zone height 353 is below the middle of the characteristic height 352 of the semiconductive well 310. In an embodiment, the virtual depletion zone height 353 is above the middle of the characteristic height 352 of the semiconductive well 310. Consequently, a non-symmetrically vertically positioned virtual semiconductor nanowire exists in the form of the virtual depletion zone 315 that has been imposed within the patterned depletion zone 312

In an embodiment, the aspect ratio of the virtual depletion zone 315 is affected by gate voltage within the bottom gate 330 as well as the other gates 320, 322, and the top gate. As depicted in FIG. 3b, the aspect ratio of the virtual depletion zone 315 is a flattened oval such that the second width 318 if it is unity is greater than a virtual depletion zone height 319. Consequently, the aspect ratio, height divided by width, is less than one. In an embodiment, the aspect ratio is equal to one. In an embodiment, the aspect ratio is greater than one. Aspect ratio is also measured by a comparison of at least one of current and potential in the lateral gates 320 and 322 to at least one of the current and potential in the top gate and the bottom gate 330.

In an embodiment, a non-symmetrically vertically positioned and eccentric virtual semiconductor nanowire exists in the form of the virtual depletion zone 315 that has been imposed within the patterned depletion zone 312. Consequently, the location of the virtual depletion zone 315 is programmable. Further, the effective size of the virtual depletion zone 315 is also programmable. In a method embodiment, an FET is first operated and checked against a standard. Next, the virtual depletion zone, e.g., virtual depletion zone 315 is second established in a different area of the well and checked against both the standard and the first virtual depletion zone. As a result, the practical screening of the location and effective size of the virtual depletion zone 315 can lead to a more useful signal-to-noise ratio because ion penetration into the conductive channel reduces the noise.

By reading this disclosure, one of ordinary skill in the art will appreciate the virtual nanowire can be constructed in any of several field-effect transistor structures, including gate all around (GAA) FET, a quadruple gate FET, a four-gate FET, a pi gate FET, a cylindrical gate FET, an omega gate FET, a triple gate FET, and fin FET.

Figure 4:
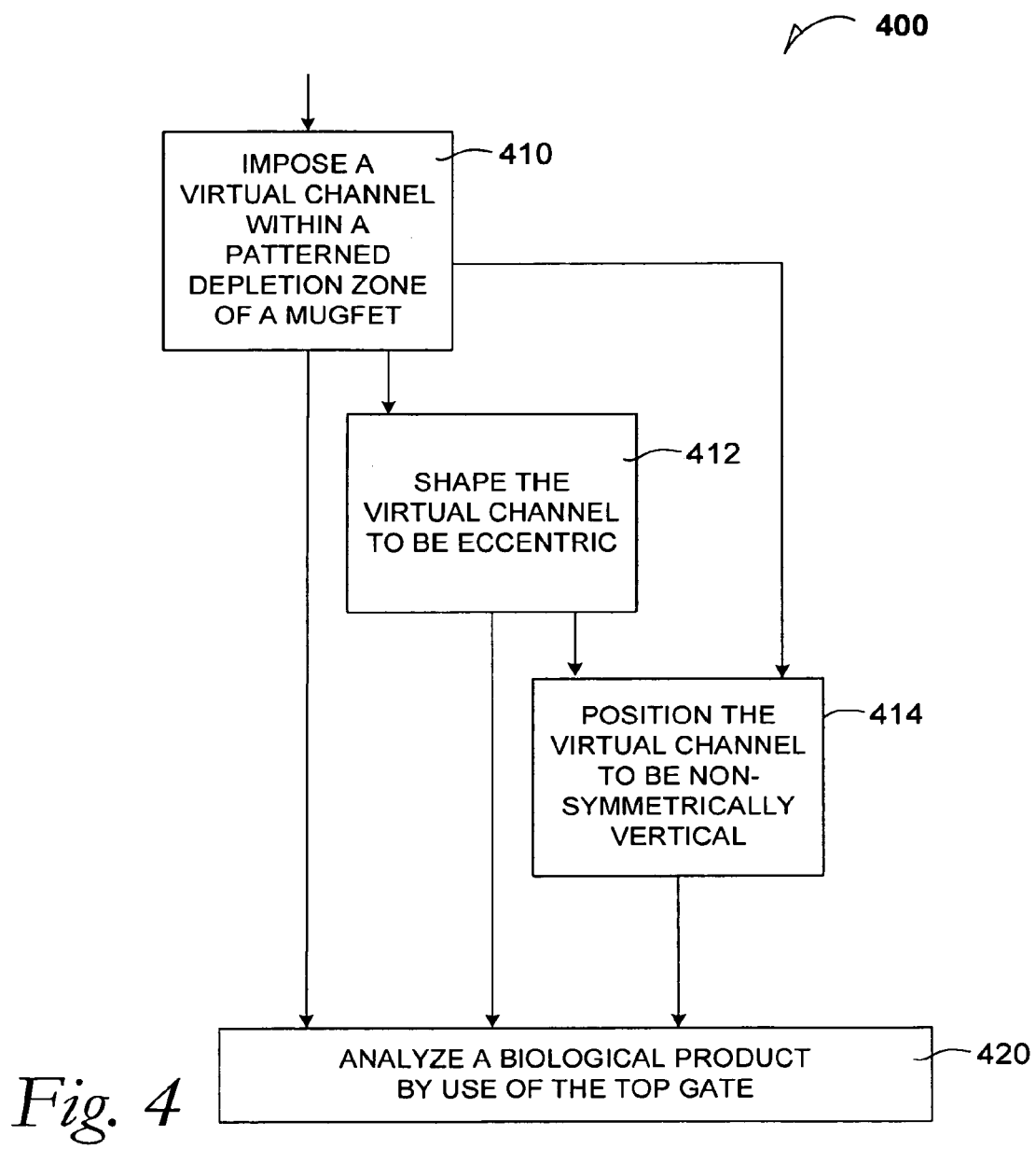
FIG. 4 is a method flow diagram 400 according to an embodiment.

FIG. 4 is a method flow diagram 400 according to an embodiment.

At 410, the method includes imposing a virtual channel within a patterned depletion zone of a MUGFET.

At 412, the method includes shaping the virtual channel to be eccentric. In an embodiment, shaping is done to achieve a more useful virtual channel such that a greater sensitivity is achieved than without shaping. In an embodiment, the method commences at 410, passes through 412, and terminates at 420.

At 414, the method includes positioning the virtual channel to be non-symmetrically vertical. In an embodiment, the method commences at 410, passes through 414, and terminates at 420. In an embodiment, the method commences at 410, passes through each of 412 and 414, and terminates at 420.

At 420, the method includes analyzing a biological product by use of the top gate of the MUGFET. As set forth in this disclosure, analysis may include a label-free protein analysis method is achieved by using a MUGFET embodiment that uses a fluid portion of a top gate that carries an analyte of the biological product.

Figure 5:
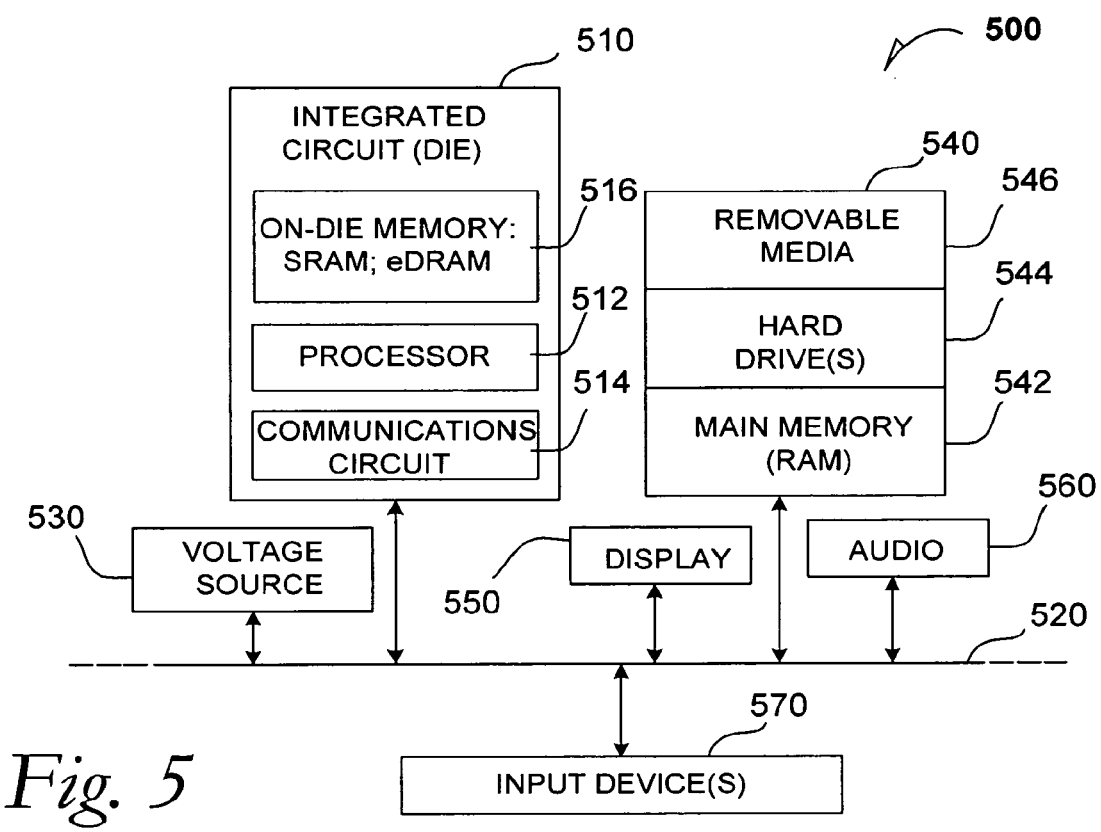
FIG. 5 is a schematic of an electronic system according to an embodiment.

FIG. 5 is a schematic of an electronic system 500 according to an embodiment. The electronic system 500 as depicted can embody a MUGFET with a fluid top electrode and a virtual channel computing system as set forth in this disclosure. In an embodiment, the electronic system 500 is a computer system that includes a system bus 520 to electrically couple the various components of the electronic system 500. The system bus 520 is a single bus or any combination of busses according to various embodiments. The electronic system 500 includes a voltage source 530 that provides power to the integrated circuit 510. In some embodiments, the voltage source 530 supplies current to the integrated circuit 510 through the system bus 520.

The integrated circuit 510 is electrically coupled to the system bus 520 and includes any circuit, or combination of circuits according to an embodiment. In an embodiment, the integrated circuit 510 includes a processor 512 that can be of any type. As used herein, the processor 512 may mean any type of circuit such as, but not limited to, a microprocessor, a microcontroller, a graphics processor, a digital signal processor, or another processor. Other types of circuits that can be included in the integrated circuit 510 are a custom circuit or an ASIC, such as a communications circuit 514 for use in wireless devices such as cellular telephones, pagers, portable computers, two-way radios, and similar electronic systems. In an embodiment, the processor 510 includes on-die memory 516 such as SRAM. In an embodiment, the processor 510 includes on-die memory 516 such as eDRAM.

In an embodiment, the electronic system 500 also includes an external memory 840 that in turn may include one or more memory elements suitable to the particular application, such as a main memory 542 in the form of RAM, one or more hard drives 544, and/or one or more drives that handle removable media 546, such as diskettes, compact disks (CDs), digital video disks (DVDs), flash memory keys, and other removable media known in the art.

In an embodiment, the electronic system 500 also includes a display device 550, an audio output 560. In an embodiment, the electronic system 500 includes a controller 570, such as a keyboard, mouse, trackball, game controller, microphone, voice-recognition device, or any other device that inputs information into the electronic system 500.

As shown herein, the integrated circuit 510 can be implemented in a number of different embodiments, including an electronic package, an electronic system, a computer system, one or more methods of fabricating an integrated circuit, and one or more methods of fabricating an electronic assembly that includes the integrated circuit and the virtual nanowire MUGFET chip as set forth herein in the various embodiments and their art-recognized equivalents. The elements, materials, geometries, dimensions, and sequence of operations can all be varied to suit particular packaging requirements.

The Abstract is provided to comply with 37 C.F.R. §1.72(b) requiring an abstract that will allow the reader to quickly ascertain the nature and gist of the technical disclosure. It is submitted with the understanding that it will not be used to interpret or limit the scope or meaning of the claims.

In the foregoing Detailed Description, various features are grouped together in a single embodiment for the purpose of streamlining the disclosure. This method of disclosure is not to be interpreted as reflecting an intention that the claimed embodiments of the invention require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate preferred embodiment.

It will be readily understood to those skilled in the art that various other changes in the details, material, and arrangements of the parts and method stages which have been described and illustrated in order to explain the nature of this invention may be made without departing from the principles and scope of the invention as expressed in the subjoined claims.

What is claimed is:

1. A method comprising:
analyzing a biological product at a top gate of a multiple-gate field-effect transistor (MUGFET), wherein the MUGFET includes:
a first lateral gate and a second lateral gate disposed on opposite sides of a semiconductive well;
a top gate and a bottom gate disposed respectively above and below the semiconductive well, wherein the top gate contains a capture molecule disposed within the top gate and an electrically conductive fluid to receive a biological product and;
a source region and a drain region disposed on opposite sides of the semiconductive well;

a patterned depletion zone between the first and second lateral gates, wherein the patterned depletion zone includes a first width; and a virtual depletion zone imposed in the semiconductive well, wherein the virtual depletion zone includes a second width that is less than the first width, and wherein analyzing includes detecting a voltage proportional to the presence of the biological product in the electrically conductive fluid of the top gate.

2. The method of claim 1, wherein analyzing includes first imposing the virtual depletion zone into an eccentric shape within the semiconductive well.

3. The method of claim 1, wherein analyzing includes first imposing the virtual depletion zone as a non-symmetrically vertically imposed depletions zone within the semiconductive well.

4. The method of claim 1, wherein analyzing includes first imposing the virtual depletion zone into a non-symmetrical shape within the semiconductive well and imposing the virtual depletion zone as a non-symmetrically vertically imposed depletions zone within the semiconductive well.

5. The method of claim 1, wherein analyzing includes monitoring at least one of potential and current within the virtual depletion zone.

* * * * *